US 6,748,950 B2

(12) United States Patent
Clark et al.

(10) Patent No.: US 6,748,950 B2
(45) Date of Patent: Jun. 15, 2004

(54) COMPOSITIONS AND MEDICAL PROCEDURE TO TREAT SNORING

(75) Inventors: Jeffrey G. Clark, Raleigh, NC (US); Anthony J. Sherbondy, Raleigh, NC (US)

(73) Assignee: Closure Medical Corporation, Releigh, NC (US)

( * ) Notice: Subject to any disclaimer, the term of this patent is extended or adjusted under 35 U.S.C. 154(b) by 438 days.

(21) Appl. No.: 09/843,774

(22) Filed: Apr. 30, 2001

(65) Prior Publication Data

US 2002/0157675 A1 Oct. 31, 2002

(51) Int. Cl.⁷ .................................................. A61F 5/56
(52) U.S. Cl. ........................ 128/848; 602/902; 128/898
(58) Field of Search ................................ 128/846, 848, 128/859–862; 602/902; 433/6

(56) References Cited

U.S. PATENT DOCUMENTS

| 2,271,858 A | 2/1942 | Galvao |
| 3,254,111 A | 5/1966 | Hawkins et al. |
| 3,995,641 A | 12/1976 | Kronenthal et al. |
| 4,364,876 A | 12/1982 | Kimura et al. |
| 4,876,283 A | * 10/1989 | Reichert ........................ 514/562 |
| 5,514,371 A | 5/1996 | Leung et al. |
| 5,514,372 A | 5/1996 | Leung et al. |
| 5,575,997 A | 11/1996 | Leung et al. |
| 5,582,834 A | 12/1996 | Leung et al. |
| 5,624,669 A | 4/1997 | Leung et al. |
| 6,187,318 B1 | * 2/2001 | Mitchell ...................... 424/195.1 |
| 6,250,307 B1 | * 6/2001 | Conrad ........................... 128/898 |
| 6,546,936 B2 | * 4/2003 | Knudson ........................ 128/898 |
| 6,579,469 B1 | * 6/2003 | Nicholson et al. ........... 252/182.11 |

OTHER PUBLICATIONS

Philip D. Littlefield and Eric A. Mair, "Snoring surgery: Which one is best for you?", *ENT–Ear Nose & Throat Journal*, vol. 78, No. 11, pp. 861–870 (Nov. 1999).

* cited by examiner

Primary Examiner—Michael A. Brown
(74) Attorney, Agent, or Firm—Oliff & Berridge, PLC

(57) ABSTRACT

A method of treating snoring, includes injecting least one of a monomer composition, a polymer solution and a microparticle solution into a patient's soft palate, optionally with a least one of an additional medicament, bioactive agent, sclerotic agent or stiffening agent. The injected composition, if not already polymerized prior to injection, is allowed to polymerize to form a polymer within the soft palate, thereby stiffening the soft palate, rendering it resistant to palatal flutter.

49 Claims, No Drawings

COMPOSITIONS AND MEDICAL PROCEDURE TO TREAT SNORING

BACKGROUND OF THE INVENTION

1. Field of Invention

The present invention relates to compositions, materials and methods for the treatment of snoring.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

U.S. Pat. Nos. 5,514,371, 5,514,372, 5,575,997, 5,624,669, and 5,582,834 to Leung et al. disclose the addition of a therapeutic agent in a cyanoacrylate composition. The cyanoacrylate adhesive forms a matrix for the therapeutic agent, with the therapeutic agent being released in vivo over time from the matrix during biodegradation of the polymer.

Despite the widespread use of cyanoacrylate adhesives for medical and industrial purposes, to date, cyanoacrylate adhesives have not been used to treat patients suffering from snoring. Excessive snoring affects nearly 20% of all adults, and nearly 50% of adults over the age of 60 are chronic snorers. Snoring is caused by a variety of factors including, but not limited to, lack of exercise, obesity, alcohol consumption and smoking. Generally, snoring is due to airway obstruction. As a result, minor snoring is caused by minimal airway obstruction. Similarly, more severe snoring, at its worst, can be caused by complete airway obstruction which can lead to obstructive sleep apnea syndrome (OSAS). Individuals who suffer from OSAS experience excessive airway obstruction that can lead to sleep fragmentation and even excessive daytime sleepiness (EDS).

Physicians often treat minor snoring by recommending that patients take simple measures such as increasing exercise, losing weight, decreasing alcohol consumption, reducing smoking, altering sleeping position, and using dental or nasal appliances. Although these relatively simple measures can be somewhat effective, many patients do not experience satisfactory relief from snoring. As a result, for many patients the only alternative is surgery.

Several surgical methods have been developed to reduce snoring. Among the various known methods, the most common methods involve surgical procedures performed to the palate, the rectopalatal pharynx, retrolingual pharynx, and the nasal passages. Generally, palatal surgical procedures are the least invasive and most widely used surgical procedures.

One of the earliest surgical procedures developed, which is still in use today, is uvulopalatopharygoplasty (UPPP). This procedure was developed in 1961 and was first introduced in the United States in 1981 to treat OSAS, and later to treat snoring in general. In this procedure a physician performs a tonsillectomy, and then partially removes the soft palate and pharyngeal arches. Finally, the mucosal edges are approximated with sutures. The objective of this procedure is to reduce snoring by providing additional room for airflow and reducing the amount of vibratory tissue.

Although UPPP is initially 75 to 100% effective in eliminating or at least reducing snoring, the long term success rates of UPPP are not as promising. More specifically, studies show that 13% of patients who have "successful" outcomes develop a recurrence of snoring within a period of one year from the date of the surgery. Overall, studies indicate that only 46% of patients report complete prevention or significant reduction of snoring over time.

In addition to the poor success rates of UPPP, various complications can also occur as a result of the procedure. The most serious complication is a 2 to 11% incidence of postoperative airway obstruction resulting in a 1% perioperative mortality. In addition, 2 to 5% of patients experience serious postoperative bleeding that requires the patients to return for further medical treatment. Many patients also report severe postoperative pain. In one study, of 86% of patients who reported a successful outcome, only 60% of those patients indicated that they would be willing to undergo the same treatment despite the resulting postoperative pain.

The most common long-term complications associated with UPPP include velopharyngeal incompetence (VPI) and palatal dryness. Most patients experience at least temporary postoperative VPI. In addition, 10 to 24% of patients report intermittent nasopharyngeal regurgitation one year after surgery. In similar studies, up to 31% of patients reported persistent palatal dryness. Less frequent long-term complications can include nasopharyngeal stenosis, long-term voice changes and partial loss of taste.

In addition to the many drawbacks associated with UPPP, UPPP is also an expensive procedure. Although the cost of the procedure can vary significantly, generally the procedure, the anesthesia and one night of postoperative observation in an intensive care unit can exceed $10,000.

In view of the obvious disadvantages of UPPP, efforts were made to develop a more effective, safer and more economical procedure. These efforts resulted in the development of laser-assisted uvuloplataplasty (LAUP). This procedure, originally referred to as laser vaporization of the palatapharynx, is similar to conventional UPPP except that it does not involve the removal of the tonsils. In addition, LAUP differs from convention UPPP because it is performed in several stages using only local anesthesia.

The most popular LAUP procedure is performed using a $CO_2$ laser having a special backstop attachment to make vertical incisions on both sides of the uvula. These incisions form trenches that extend 1 to 2 cm from the free edge of velum. The uvulum is then significantly shortened. The entire procedure is performed under local anesthesia and is repeated within 4 to 6 weeks as needed.

Initially, the results of LAUP were promising. Short term success rates were reported to be between 70 and 97%. However, as with UPPP, LAUP patients also suffered from a decrease in long-term efficiency. A study of the long-term effectiveness of LAUP showed that at 18 to 24 months following the procedure only 55% of patients reported that their bed partner was satisfied with the results of the procedure.

However, when compared with UPPP, LAUP is less invasive because it involves less palatal resection, and does not require removal of a patient's tonsils. In addition, the procedures can be performed using only local anesthesia. These differences can result in fewer postoperative complications, including postoperative bleeding and airway obstruction. In addition, by reducing the amount of palatal resection, LAUP can also reduce the likelihood of long-term complications such as VPI and voice changes.

Despite the reduction in postoperative complications, LAUP patients, like UPPP patients, still experience severe post-operative pain. In particular, studies show that patients who undergo LAUP experience no significant difference in post-operative pain from patients who undergo UPPP. However, unlike UPPP, LAUP patients must undergo the procedure and endure the resulting post-operative pain multiple times to achieve satisfactory results. Generally, LAUP patients require two to four sessions to achieve successful results.

Overall, LAUP does not differ substantially from UPPP. However, LAUP is substantially less costly than UPPP. For instance, a typical LAUP procedure is estimated to only cost between $1,500 and $2,000.

Because of the disadvantages of UPPP and LAUP, surgeons were motivated to develop simpler and less invasive procedures. Efforts to develop improved procedures resulted in the development of palatal sclerotic operations. Surgeons believed that by stiffening the soft palate, rather than merely shortening it, they could substantially reduce palatal flutter that causes snoring. Generally, surgeons proposed inducing scar formation using a laser to remove a longitudinal strip of palatal mucosa, while leaving the velum and uvulum intact.

Studies show that the short-term efficacy of palatal sclerotic procedures are similar to the efficacy of both UPPP and LAUP. However, because palatal stiffening procedures are substantially less invasive, even as compared to LAUP, they produce fewer post-operative complications. In addition, palatal stiffening procedures are more convenient and more economical than UPPP and LAUP procedures. In particular, palatal stiffening procedures can be performed during a single outpatient visit using only local anesthesia. In addition, when palatal stiffening is performed using electrocautery procedures the process can be performed without the need for expensive and cumbersome laser equipment. Also, although cost can vary among different institutions, estimates indicate that a typical palatal stiffening procedure only costs about $150. Thus, the cost of a typical palatal stiffening procedure is about ten times less than an LAUP procedure, and about seventy times less than a UPPP procedure.

Recently, a more effective palatal stiffening procedure, called radio frequency ablation (RFA), has been developed. This procedure uses a custom electrode to delivery radio frequency energy to the soft palate. In a study RFA decreased snoring 77% after three to four treatments. In addition, patients who underwent RFA suffered no major complications. The only minor complication reported was erosion of the palatal surface mucosa two to four days after treatment.

The advantage of RFA over UPPP and LAUP is that RFA is substantially less invasive, and thereby reduces the incidence of post-operative complications. Also, because RFA stiffens the soft palate by scarring the palatal muscle, generally leaving the palatal mucosa unaffected, RFA can be substantially less painful than other more invasive procedures.

Also, like other palatal stiffening procedures RFA is performed using only local anesthesia. Unfortunately, like other palatal stiffening procedures, RFA must be performed multiple times to obtain satisfactory results. During the administration of anesthetic, one must be careful to insert the needle directly into the palatal muscle to avoid mucosal sloughing that can occur as a result of inaccurate needle insertion. In addition, RFA requires expensive equipment, including a radio frequency generator and disposable hand pieces. Overall, the cost of an RFA procedure is about $2,500.

The above described surgical techniques are described in greater detail in conjunction with figures in "Snoring surgery: Which one is best for you?", ENT-Ear Nose & Throat Journal, Volume 78, Number 11, Pages 861–870 (November 1999), written by Philip D. Littlefield and Eric A. Mair, which is incorporated herein by reference in its entirety.

As a result, even though the procedures for treating snoring have improved, there remains a need for a procedure that is not only non-invasive and economical, but that also ensures long-term reduction and/or elimination of snoring.

SUMMARY OF THE INVENTION

The present invention is directed to an improved palatal stiffening composition or solution and a procedure using such a composition or solution for reduction and/or elimination, and preferably long-term reduction and/or elimination, of snoring. The procedure of the present invention comprises injecting at least one of a polymerizable monomer composition, a polymer composition, and a microparticle solution into a patient's soft palate to stiffen the soft palate, thereby reducing or substantially eliminating palatal flutter. The procedure of the present invention is not only minimally invasive and economical, but also provides long-term relief from snoring.

DETAILED DESCRIPTION OF PREFERRED EMBODIMENTS

This invention is directed to compositions and methods for treating snoring by injecting at least one of a polymerizable monomer composition, a polymer solution or a microparticle solution into a patient's soft palate to reduce palatal flutter by stiffing the patient's soft palate.

According to embodiments of the present invention, the composition or solution can be injected alone, or it can be injected together with at least one of a medicament, a bioactive agent, a sclerotic agent, and a stiffening agent. Furthermore, in embodiments, the composition or solution can itself include one or more medicaments, bioactive agents, sclerotic agents, and stiffening agents. Moreover, in embodiments, a single medicament or agent can provide a medicinal/bioactive effect as a primary effect and a sclerotic and/or stiffening effect as a secondary effect. In addition, in other embodiments comprising microparticles, the primary effect of the microparticles can be sclerotic and/or stiffening while the secondary effect can be a medicinal or bioactive effect. In other words, while the microparticles may primarily cause scar tissue formation and/or stiffening, thus serving a sclerotic and/or stiffening purpose, the microparticles may also provide a secondary medicinal or bioactive purpose. Thus, in various embodiments, a single composition can provide both a medicinal/bioactive effect and a sclerotic/stiffening effect.

In embodiments of the invention, a topical anesthetic can be administered to a patient's soft palate at least one of before, during or after injection of the composition or solution. Generally, various known methods and devices can be used to inject the composition of the present invention. Suitable injection devices include, but are not limited to, hypodermic needles, pneumatic $CO_2$ injectors, and the like. One suitable injection device is a ¾ inch 27 gauge needle bent at a 30–45 degree angle. Regardless of the method or apparatus used to inject the composition, care should be taken to ensure that the injection is made accurately to avoid injecting the composition into unintended regions.

Preferably, the composition is injected in a sufficient amount to stiffen the soft palate in order to substantially reduce and/or eliminate soft palate flutter that can cause snoring. In embodiments, depending upon the size and condition of a patent's soft palate, the amount of composition injected ranges from between about 0.1 cc to about 5 cc, about 0.25 cc to about 3 cc or from about 0.5 cc to about 3 cc.

The composition and treatment method of the present invention provide significantly longer relief from snoring than conventional snoring treatment procedures. More specifically, the inventors of the present invention estimate, based on the flexibility and longevity of the monomer compositions, polymer solutions and microparticle solutions of the present invention, that the method of the present invention will reduce or eliminate snoring for a duration of at least about 12 months, or more. Ideally, the monomer composition of the present invention will provide sufficient flexibility and longevity to substantially reduce or eliminate snoring indefinitely.

In embodiments of the present invention where a polymerizable monomer composition is injected into a patient's soft palate, the composition can include various known polymerizable monomers. Suitable compositions can include one or more polymerizable monomers. Preferred monomers that may be used in the present invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. Nos. 5,32,687, and 5,928,611 to Leung et al., U.S. patent application Ser. No. 09/430,177, filed on Oct. 29, 1999, and U.S. patent application Ser. No. 09/471,392 filed on Dec. 23, 1999, which are hereby incorporated in their entirety by reference herein. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 2 to about 12 or more, and more preferably from about 3 to 8 carbon atoms.

The α-cyanoacrylates of the present invention can be prepared according to several methods known in the art. U.S. Pat. Nos. 2,271,858, 3,254,111, 3,995,641, and 4,364, 876, each of which is hereby incorporated in its entirety by reference herein, disclose methods for preparing α-cyanoacrylates.

In embodiments of the present invention where a polymer solution is injected into a patient's soft palate, the composition can include various polymers. Suitable polymers include, but are not limited to, polymers formed partially, substantially, or entirely from 1,1-disubstituted monomers, such as those described above. Preferred polymers in embodiments are non-degradable polymers. Suitable polymers can be either biodegradable, temporary polymers, or non-biodegradable, more permanent polymers. In the event that a degradable polymer is used, it is preferred that the polymer degrade no faster than six months, although the degradation time could be suitably selected to obtain desired results.

In embodiments where a polymer solution is injected, the polymer solution can comprise the desired polymer in a suitable non-polymerizable carrier, or can comprise the desired polymer in a solution of polymerizable monomer material. Thus, for example, the injectable composition can include a first component that is a polymer material and a second component that is a polymerizable monomer material, which can be the same as or different from monomer units of the polymer material. In this embodiment, it is preferred that the monomer composition preferably be comprised of 1,1-disubstituted monomers, such as those described above. In addition, in embodiments of the present invention where a solution of microparticles is injected into a patient's soft palate, the solution can include various types of microparticles. Suitable microparticles include, but are not limited to, microparticles composed of polymers, glass, ceramics, pyrolytic carbon or metals. The microparticles can have a variety of particle shapes and sizes. In particular, the average particle size of microparticles in a solution of the present invention can be from about 0.5 $\mu$m to about 200 $\mu$m, preferably from about 0.1 $\mu$m to about 200 $\mu$m, more preferably from about 0.25 $\mu$m to about 100 $\mu$m and more preferably from about 0.5 $\mu$m to about 50 $\mu$m. In addition, the composition of the present invention may comprise a combination of monomers, polymers and microparticles. In preferred embodiments, the composition of the present invention can include a combination of monomer and microparticles or a combination of polymer and microparticles.

According to the present invention, in embodiments where a polymerizable monomer composition is injected, the composition is preferably permitted to begin polymerizing during injection or after being injected. Once polymerized, the injected monomer composition renders the soft palate substantially rigid and resistant to flutter that can occur as air flows over a patient's soft palate during breathing.

In further embodiments of the present invention, the injected composition can be injected together with, before, or after a medicament, a bioactive agent, a sclerotic agent, or a stiffening agent. The medicament or agent in this embodiment is not particularly limited, and can include any of the available medicaments, bioactive agents, sclerotic agents or stiffening agents for anesthetizing, medicating or enhancing the stiffening of the soft palate, provided that the medicament or agent is not incompatible with the injected composition. One suitable anesthetic is benzocaine. In addition, suitable sclerotic agents include, but are not limited to, sodium tetradecyl sulfate (Sotradecol®), ethyl alcohol, tetracycline, and doxycycline. In one embodiment, the medicament, sclerotic agent or stiffening agent can be first applied or injected into the soft palate area, followed by injection of the composition. The medicament or agent can be in any suitable form, including liquid, solid, powder, cream or the like, and can include only a medicament or can include other suitable bioactive agents, sclerotic agents, stiffening agents, carriers, additives, mixtures thereof, and the like.

In other embodiments of the present invention, an appropriate, compatible, medicament, bioactive agent, sclerotic agent or stiffening agent can be mixed with the injected composition and a resultant composition injected into the soft palate. In this embodiment, the medicament or agent can be mixed with the composition or solution during manufacture (i.e. prior to packaging the materials), immediately prior to use or during the injection itself.

Also, in other embodiments, a compatible medicament, bioactive agent, sclerotic agent or stiffening agent can be injected after the composition or solution has been injected. In such embodiments, the injected medicament or agent can mix with the previously injected composition or can serve its intended function without intermixing with the injected composition.

In further embodiments of the present invention, the medicament or agent can also serve as a polymerization initiator or a stabilizer. Thus, the medicament or agent can provide not only a biological or a physiological activity, but a chemical one as well.

Medicaments and/or agents that also serve as polymerization initiators can initiate and/or accelerate the polymerization of an injected monomer composition when injected into a soft palate region. Accelerated polymerization reduces the waiting time necessary after injection, and makes the composition more convenient to administer. Suitable medicaments and agents that can also serve as initiators include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; ascorbic acid; tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

In preferred embodiments, the initiator may be a bioactive material, including quaternary ammonium halides such as alkylbenzyldimethylammonium chloride (benzalkonium chloride; BAC) its pure components, or mixtures thereof, especially those with an alkyl containing 6–18 carbon atoms; benzethonium chloride; and salts of sulfadiazine. Cobalt napthenate can be used as an accelerator for peroxide.

In preferred embodiments, the initiator may be a bioactive material that possesses antiviral, antimicrobial, antifungal and/or wound healing properties. An example of such a material that possesses polymerization initiation and antiviral, antimicrobial, and/or antifungal properties is Gentian Violet, also known as crystal violet or methylrosaniline chloride. Examples of materials that possess polymerization initiation and wound healing properties also include various zinc complexes and zinc salts, antioxidants such as vitamin E and other vitamins and the like, and copper compounds such as copper chloride, copper sulfate and copper peptides, as described in "Copper: An Essential Element for Life," ProCyte Corporation, available at http://www.humatech.com/technology.html (Oct. 28, 1999), the entire disclosure of which is incorporated herein by reference. Such materials are particularly preferred because they can serve not only as the polymerization initiator or rate modifier for the cyanoacrylate monomer, they can also provide additional benefits to the wound site, such as antiviral effects, antimicrobial effects and/or antifungal effects or help to promote wound healing.

In embodiments where the medicament or agent also acts as a polymerization initiator or rate modifier, the present invention provides the additional advantage of not requiring that a further, separate polymerization initiator or rate modifier be used. Furthermore, in these embodiments, the medicament or agent is preferably located in a non-contacting relationship with the composition prior to injection, so that premature polymerization of the composition does not occur.

Medicaments and/or agents that also serve as stabilizers can extend the useful life of the composition. By increasing the useful life of the composition, the composition can be stored and packaged for longer periods of time without the risk of premature polymerization. In embodiments where the medicament or agent also acts as a stabilizer for the composition, the present invention provides the additional advantage of not requiring that a further, separate stabilizer be used. Furthermore, in these embodiments, the medicament or agent is preferably located in a contacting relationship with the composition, such as being mixed with the adhesive composition, prior to injection.

Although a mixture of medicament and/or agent and an injected composition, according to the present invention, is not limited to a specific ratio of medicament or agent to composition, the medicament or agent is preferably present in an amount to be therapeutic upon release.

When mixed immediately prior to use, the medicament or agent can be mixed with the composition in a suitable container and thereafter injected. Alternatively, mixing can be conducted during the injection process, for example, by using an injector that is loaded with medicament or agent, which thereby mixes the medicament or agent with the composition during injection.

Suitable medicaments and agents include, but are not limited to, known medicaments and agents such as anesthetics, including, but not limited to, lidocaine, sclerotic and/or stiffening agents including, but not limited to, alcohols, methyl cyanoacrylate, mixtures thereof, and the like.

In embodiments, the composition and/or its packaging are preferably sterilized. Sterilization of the composition and/or its packaging can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. Pat. No. 6,143,805, the entire disclosure of which is incorporated herein by reference. The composition should also show low levels of toxicity to living tissue during its useful life. In preferred embodiments of the present invention, the composition is sterilized to provide a Sterility Assurance Level (SAL) of at least $10^{-3}$. The Sterility Assurance Level measurement standard is described, for example, in ISO/CD 14937, the entire disclosure of which is incorporated herein by reference. In embodiments, the Sterility Assurance Level may be at least $10^{-4}$, or may be at least $10^{-5}$, or may be at least $10^{-6}$.

The composition or solution (i.e. the polymer solution system and polymerizable monomer but not the microparticle solution) of the present invention may optionally include at least one plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to tributyl citrate, acetyl tri-n-butyl citrate (ATBC), polymethylmethacrylate, polydimethylsiloxane, hexadimethylsilazane and others as listed in U.S. patent application Ser. No. 09/471,392 filed Dec. 23, 1999, the disclosure of which is incorporated in its entirety by reference herein.

The composition or solution of the present invention may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. patent application Ser. No. 09/374,207 filed Aug. 12, 1999, the disclosures of which are hereby incorporated in their entireties by reference herein.

The composition or solution of the present invention may optionally also include thickeners. Suitable thickeners may include poly (2-ethylhexy methacrylate), poly(2-ethylhexyl acrylate) and others as listed in U.S. patent application Ser. No. 09/472,392 filed Dec. 23, 1999, the disclosure of which is incorporated by reference herein in its entirety.

The composition or solution of the present invention may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition or solution of the present invention may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. patent application Ser. No. 09/471,392 filed on Dec. 23, 1999, the disclosure of which is incorporated by reference herein in its entirety. Furthermore, certain stabilizers may also function as bioactive agents, sclerotic agents or stiffening agents, such as, for example, various compounds including, but not limited to the above-identified compounds.

The stability, and thus the shelf-life, of some monomeric adhesive compositions can be further enhanced and extended through careful regulation of the packaging. Treated (e.g., fluorinated polymer) packaging such as that disclosed in copending U.S. patent application Ser. No. 09/430,289, filed Oct. 29, 1999, which is hereby incorporated by reference herein in its entirety, is preferred and may reduce the amount of stabilizer that is combined into the composition. As mentioned above, certain stabilizers including, but not limited to, the above-identified compounds, can also function as bioactive agents, sclerotic agents or stiffening agents. In this case, the amount of the agent/stabilizer material is either not reduced below a level to provide the desired biological or physiological effect, or a further bioactive agent, sclerotic agent or stiffening agent is added to ensure that the desired biological or physiological effect is obtained.

The compositions of the present invention may also include pH modifiers to control the rate of degradation of the resulting polymer, as disclosed in U.S. patent application Ser. No. 08/714,288, filed Sep. 18, 1996, the entire disclosure of which is hereby incorporated by reference herein in its entirety.

Compositions or solutions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, all to Leung et al., which are hereby incorporated herein by reference in their entireties.

To improve the cohesive strength of the compositions or solutions of this invention, difunctional monomeric cross-linking agents may be added to monomer compositions of this invention. Such crosslinking agents are known. U.S. Pat. No. 3,940,362 to Overhults, which is hereby incorporated herein in its entirety by reference, discloses exemplary cross-linking agents.

The compositions or solutions of this invention may further contain fibrous reinforcement and colorants such as dyes, pigments, and pigment dyes. Examples of suitable fibrous reinforcement include PGA microfibrils, collagen microfibrils, and others as described in U.S. patent application Ser. No. 09/471,392 filed on Dec. 23, 1999, the disclosure of which is incorporated by reference herein in its entirety.

The polymerizable compositions useful in the present invention may also further contain one or more preservatives, for prolonging the storage life of the composition. Suitable preservatives, and methods for selecting them and incorporating them into adhesive compositions, are disclosed in U.S. patent application Ser. No. 09/430,180, the entire disclosure of which is incorporated herein by reference. Such preservatives can be in addition to any anti-fungal agent that may or may not be added to the composition, as described above.

In embodiments of the present invention, the composition or solution and/or its injector may contain materials such as a polymerization initiator, accelerator, rate-modifier, and/or cross-linking agent for initiating polymerization and/or cross-linking of the polymerizable monomer material. Suitable materials and packaging systems are disclosed in U.S. Pat. No. 5,928,611 and U.S. patent applications Ser. Nos. 09/430,177, 09/430,176, 09/430,289, 09/430,290, and 09/430,180 filed Oct. 29, 1999; 09/343,914 filed Jun. 30, 1999; 09/385,030 filed Aug. 30, 1999; and 09/176,889 filed Oct. 22, 1998; the entire disclosures of which are incorporated herein by reference.

The present invention is also directed to a kit comprising at least a composition or solution and an injector to inject the composition or solution into a patient's soft palate. In an exemplary embodiment, the kit can contain at least one of a monomer composition, a polymer composition and a microparticle solution in a storage container, a swab for drying the palate prior to injection or for removing excess composition during or after injection, and an injector to inject the composition or solution. In an exemplary embodiment, that injector can be a hypodermic needle. The kit of the present invention may also include one or more of a plasticizer, a stabilizer, a medicament, a sclerotic agent, a stiffening agent, bioactive agent and a polymerization initiator. The at least one plasticizer, stabilizer, medicament, sclerotic agent, stiffening agent, bioactive agent and polymerization initiator can be separate from the composition or solution, such as in a separate storage container within the kit, or pre-mixed together with the composition or solution prior to injection.

EXAMPLES

Example 1

A formulated 2-octyl cyanoacrylate monomer composition is used to treat palatal flutter in a beagle. Prior to treatment for palatal flutter, the palatal flutter of the beagle is measured to be 65–70 per minute.

The composition is then injected into the beagle's soft palate. Following injection, but prior to complete polymerization of the monomer composition, the injection site is massaged so as to form a plane of monomer material, rather than a bulb of material. The monomer composition polymerizes, resulting in a polymerized material within the soft palate. The polymerized material substantially stiffens the soft palate, rendering it resistant to flutter. After treatment for palatal flutter, the palatal flutter of the beagle is measured to be 0 per minute.

While the invention has been described with reference to preferred embodiments, the invention is not limited to the specific examples given, and other embodiments and modifications can be made by those skilled in the art without departing from the spirit and scope of the invention.

What is claimed is:

1. A method of treating snoring, comprising:
   injecting a composition selected from the group consisting of a polymerizable monomer composition, a polymer solution, a microparticle solution, and mixtures thereof, into a patient's soft palate, thereby stiffening the soft palate with the injected composition to reduce palatal flutter.

2. The method of claim 1, wherein said composition is a polymerizable monomer composition.

3. The method of claim 2, further comprising allowing said polymerizable monomer composition to polymerize to form a polymer within the soft palate at least one of during or after injection.

4. The method of claim 2, wherein said composition comprises a 1,1-disubstituted ethylene monomer.

5. The method of claim 2, wherein said composition comprises an α-cyanoacrylate monomer.

6. The method of claim 2, wherein said composition comprises at least one member selected from the group consisting of ethyl cyanoacrylate, butyl cyanoacrylate, and 2-octyl cyanoacrylate.

7. The method of claim 2, further comprising injecting at least one of a cyanoacrylate-compatible medicament, bioactive agent, sclerotic agent or stiffening agent together with said composition into the soft palate so that the at least one medicament or agent serves as a polymerization initiator for said composition.

8. The method of claim 2, wherein said composition comprises at least one stabilizing agent.

9. The method of claim 8, wherein said stabilizing agent is also at least one of a medicament, a bioactive agent, a sclerotic agent, or a stiffening agent.

10. The method of claim 1, wherein said composition further comprises at least one of a cyanoacrylate-compatible medicament, bioactive agent, sclerotic agent or stiffening agent.

11. The method of claim 2, wherein said composition comprises at least one plasticizer.

12. The method of claim 11, wherein the plasticizer is selected from the group consisting of tributyl citrate, acetyl tributyl citrate, polymethylmethacrylate, polydimethylsiloxane and hexadimethylsilazane.

13. The method of claim 1, wherein said composition is a polymer solution.

14. The method of claim 1, wherein said composition is a microparticle solution.

15. The method of claim 14, wherein said microparticle solution comprises microparticles made of a material selected from the group consisting of a polymer, a glass, a ceramic, and a metal.

16. The method of claim 1, wherein said composition is a combination of a polymerizable monomer and a microparticle solution.

17. The method of claim 1, wherein said composition is a combination of a polymer solution and a microparticle solution.

18. The method of claim 1, wherein the said composition further comprises at least one of a medicament, a bioactive agent, a sclerotic agent, or a stiffening agent.

19. The method of claim 18, wherein the at least one medicament, bioactive agent, sclerotic agent or stiffening agent is mixed with said composition immediately prior to injecting said composition to the soft palate.

20. The method of claim 18, wherein the at least one medicament, bioactive agent, sclerotic agent or stiffening agent is mixed with said composition during manufacture of said composition.

21. The method of claim 1, wherein said composition has a Sterility Assurance Level (SAL) of $10^{-3}$–$10^{-6}$.

22. The method of claim 1, further comprising injecting at least one of a medicament, a bioactive agent, a sclerotic agent or stiffening agent into the soft palate at least one of before, during or after injecting said composition.

23. The method of claim 1, further comprising sterilizing said composition prior to injecting said composition into the soft palate.

24. The method of claim 1, further comprising sterilizing said composition using at least one sterilization method selected from the group consisting of gamma irradiation sterilization, electron beam irradiation sterilization, microwave irradiation sterilization, thermal sterilization, and chemical sterilization.

25. The method of claim 1, further comprising administering a local anesthetic to the patient's soft palate.

26. A method of treating snoring, the method comprising:
a) combining (i) a composition selected from the group consisting of a polymerizable monomeric composition, a polymeric solution and a microparticle solution with (ii) at least one of a compatible medicament, bioactive agent, sclerotic agent or stiffening agent to form a treatment mixture; and
b) injecting said treatment mixture into a patient's soft palate.

27. The method of claim 26, wherein said mixture comprises a polymerizable monomeric composition and a bioactive agent.

28. The method of claim 27, further comprising allowing said monomeric composition to polymerize to form at least one of a medicament- or agent-containing polymer within the soft palate.

29. The method of claim 28, wherein said treatment mixture is injected into the soft palate using a hypodermic needle.

30. A composition for treating snoring, the composition comprising:
at least one of a polymerizable monomer, a polymer solution and a microparticle solution, and at least one sclerotic agent or stiffening agent.

31. The composition of claim 30, wherein said sclerotic agent or stiffening agent is selected from the group consisting of sodium tetradecyl sulfate, ethyl alcohol, tetracycline, and doxycycline.

32. The composition of claim 30, wherein the composition comprises said polymerizable monomer.

33. The composition of claim 32, wherein said composition comprises a 1,1-disubstituted ethylene monomer.

34. The composition of claim 32, wherein said composition comprises an α-cyanoacrylate monomer.

35. The composition of claim 32, wherein said composition comprises at least one member selected from the group consisting of ethyl cyanoacrylate, butyl cyanoacrylate, and 2-octyl cyanoacrylate.

36. The composition of claim 32, wherein said composition further comprises at least one stabilizing agent.

37. The composition of claim 36, wherein said stabilizing agent is also at least one of a medicament, a bioactive agent, a sclerotic agent, or a stiffening agent.

38. The composition of claim 32, wherein said composition comprises at least one plasticizer.

39. The composition of claim 38, wherein the plasticizer is selected from the group consisting of tributyl citrate, acetyl tributyl citrate, polymethylmethacrylate, polydimethylsiloxane and hexadimethylsilazane.

40. The composition of claim 30, wherein the said composition further comprises at least one of a medicament and a bioactive agent.

41. The composition of claim 30, wherein said composition has a Sterility Assurance Level (SAL) of $10^{-3}$–$10^{-6}$.

42. A kit for treating snoring comprising:
a) a composition selected from the group consisting of a monomer composition, a polymer solution and a microparticle solution in a storage container;
b) at least one of a sclerotic agent and a stiffening agent; and
c) an injector for injecting said composition and said sclerotic agent or stiffening agent into a patient's soft palate.

43. The kit of claim 42, wherein said composition comprises a 1,1-disubstituted ethylene monomer.

44. The kit of claim 42, wherein said composition comprises an α-cyanoacrylate monomer.

45. The kit of claim 42, wherein said composition comprises at least one member selected form the group consisting of ethyl cyanoacrylate, butyl cyanoacrylate, and 2-octyl cyanoacrylate.

46. The kit of claim 42, wherein said injector is a hypodermic needle.

47. The kit of claim 42, wherein said sclerotic agent or stiffening agent is selected from the group consisting of sodium tetradecyl sulfate, ethyl alcohol, tetracycline, and doxycycline.

48. The kit of claim 42, wherein said sclerotic agent or stiffening agent is packaged at least one of a together with or separate from said composition.

49. The kit of claim 42, further comprising a swab.

* * * * *